(12) United States Patent
Comee et al.

(10) Patent No.: US 11,452,537 B2
(45) Date of Patent: Sep. 27, 2022

(54) MEDICAL DEVICES AND RELATED METHODS

(71) Applicant: Boston Scientific Scimed, Inc., Maple Grove, MN (US)

(72) Inventors: Shaun Comee, Fiskdale, MA (US); Christopher Deuel, Melrose, MA (US); Stanley Gilbert, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 50 days.

(21) Appl. No.: 16/515,758

(22) Filed: Jul. 18, 2019

(65) Prior Publication Data
US 2020/0022722 A1    Jan. 23, 2020

Related U.S. Application Data

(60) Provisional application No. 62/700,429, filed on Jul. 19, 2018.

(51) Int. Cl.
*A61B 17/32*    (2006.01)
*A61B 17/34*    (2006.01)

(52) U.S. Cl.
CPC .. *A61B 17/320016* (2013.01); *A61B 17/3421* (2013.01)

(58) Field of Classification Search
CPC ........ A61B 17/320016; A61B 17/3421; A61B 2010/045; A61B 17/22031; A61B 2017/320064; A61B 10/0233; A61B 10/0266; A61B 17/32053;
(Continued)

(56) References Cited

U.S. PATENT DOCUMENTS

| 6,752,769 | B2 | * | 6/2004 | Alberico | ............ | A61B 10/0266 600/564 |
| D657,461 | S | * | 4/2012 | Schembre | .......... | A61B 10/0275 D24/130 |
| 8,317,771 | B2 | | 11/2012 | Mitelberg | | |

(Continued)

FOREIGN PATENT DOCUMENTS

| WO | WO 95/08291 | 3/1995 |
| WO | WO 2014/112518 A1 | 7/2014 |
| WO | WO 2016/070059 A1 | 5/2016 |

OTHER PUBLICATIONS

PCT International Preliminary Report on Patentability dated Jan. 19, 2021, for PCT International Application No. PCT/US2019/042363.

*Primary Examiner* — Phong Son H Dang
(74) *Attorney, Agent, or Firm* — Bookoff McAndrews, PLLC

(57) ABSTRACT

According to one aspect, a medical device including a shaft having a proximal and a distal end. The medical device may also include a handle coupled to the proximal end of the shaft. The medical device may further include a body at the distal end of the shaft. The body may have a wall defining a lumen within the body, and the lumen may have a longitudinal axis. The wall may include a protrusion at the distal end of the body, and the protrusion may be defined by a gap in the wall and may have a sharp portion configured to grasp tissue. The gap may extend proximally from the distal end of the body, and edges of the wall defining the gap may be transverse to the longitudinal axis.

19 Claims, 3 Drawing Sheets

(58) Field of Classification Search
CPC ......... A61B 2017/320056; A61B 2017/32006; A61B 10/02; A61B 10/06; A61B 10/0275
See application file for complete search history.

(56) References Cited

U.S. PATENT DOCUMENTS

| | | | | |
|---|---|---|---|---|
| 8,343,073 | B2* | 1/2013 | Miller | A61B 10/0275 600/567 |
| 8,986,221 | B2* | 3/2015 | Zimmon | A61B 10/06 600/562 |
| 9,844,362 | B2* | 12/2017 | McWeeney | A61B 10/0233 |
| 9,993,231 | B2* | 6/2018 | Costello | A61B 10/0266 |
| 10,004,483 | B2* | 6/2018 | White | A61B 10/06 |
| 10,390,806 | B2* | 8/2019 | Lee | A61B 10/0096 |
| 10,820,893 | B2* | 11/2020 | Cannon | A61B 10/0266 |
| 2003/0114773 | A1* | 6/2003 | Janssens | A61B 10/0233 600/564 |
| 2004/0054377 | A1 | 3/2004 | Foster | |
| 2010/0331883 | A1 | 12/2010 | Schmitz | |
| 2012/0197157 | A1* | 8/2012 | Ryan | A61B 10/0266 600/567 |
| 2013/0131547 | A1* | 5/2013 | Hardert | A61B 10/0275 600/567 |
| 2013/0197395 | A1* | 8/2013 | Janssens | A61B 10/02 600/567 |
| 2015/0141869 | A1* | 5/2015 | Costello | A61B 10/0266 600/568 |
| 2015/0201917 | A1* | 7/2015 | Snow | A61B 10/0266 600/567 |
| 2016/0022250 | A1 | 1/2016 | Hardert | |
| 2016/0030016 | A1* | 2/2016 | McWeeney | A61B 10/0233 600/567 |
| 2016/0199047 | A1* | 7/2016 | McWeeney | A61B 8/0841 600/567 |

* cited by examiner

MEDICAL DEVICES AND RELATED METHODS

CROSS-REFERENCE TO RELATED APPLICATIONS

This application claims the benefit of priority from U.S. Provisional Application No. 62/700,429, filed on Jul. 19, 2018, which is incorporated by reference herein in its entirety.

TECHNICAL FIELD

The present disclosure relates generally to medical devices and related methods. More particularly, the present disclosure relates to various devices and methods for grasping tissue.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve grasping tissue of an organ or a gland to treat tumors, infections, and the like. Physicians often need to grasp tissue in order to take tissue samples or remove tissue from a surgical area. Conventional tissue graspers include, among other examples, rat-tooth shaped and toothed-jaw type graspers. One issue faced by these conventional devices is that tissue with a large amount of mucus has a tendency to slip from these types of tissue graspers. When tissue slips from a grasper, surgical operation times may increase and operators may need to readjust the positioning of medical devices used in a procedure because of tissue releasing from a tissue grasper.

SUMMARY

Embodiments of the present disclosure relate to, among other things, medical devices configured for grasping tissue, for use in, for example, endoscopic medical procedures. The present disclosure also relates to methods of operating the devices, and/or performing procedures with the devices. Each of the embodiments disclosed herein may include one or more of the features described in connection with any of the other disclosed embodiments.

According to one aspect, a medical device may include a shaft having a proximal and a distal end. The medical device may also include a handle coupled to the proximal end of the shaft. The medical device may further include a body at the distal end of the shaft. The body may have a wall defining a lumen within the body, and the lumen may have a longitudinal axis. The wall may include a protrusion at the distal end of the body, and the protrusion may be defined by a gap in the wall and may have a sharp portion configured to grasp tissue. The gap may extend proximally from the distal end of the body, and edges of the wall defining the gap may be transverse to the longitudinal axis.

The medical device may include one or more of the features below. The protrusion may be a first protrusion, and the body may include a second protrusion circumferentially spaced around the body from the first protrusion, and the second protrusion may be defined by a second gap in the wall and may have a second sharp portion configured to grasp tissue. The second gap may extend proximally from the distal end of the body, and edges of the wall defining the second gap may be transverse to the longitudinal axis. The gap may include a proximal section and a distal section, the distal section may extend proximally from the distal end of the body, and the proximal section may be defined by edges that extend substantially perpendicular to the longitudinal axis. The sharp portion may include a sharp point. The protrusion may include an apex formed by two surfaces meeting at an angle less than 45°. The proximal section may be defined at least partially by a rounded edge of the wall and may be configured to hold tissue. The gap in the wall may have an open distal end at a distalmost end of the body and may be defined by distalmost edges of the body. A diameter of the body at the protrusion may be the same as a diameter of the body proximal of the protrusion.

According to other aspects of the present disclosure, a medical device may include a shaft having a proximal and a distal end. The medical device may also include a tubular body at the distal end of the shaft. The tubular body may include a wall, the wall may include a protrusion at a distal end of the tubular body, and the protrusion may be defined by a slot in the wall. The slot may be transverse to a longitudinal axis of the tubular body. The slot may extend proximally from the distal end of the tubular body and may define an apex at an end of the protrusion.

The medical device may also include one or more of the features below. The apex may include a sharp point configured to pierce tissue. The slot in the wall may have an open distal end at a distalmost end of the tubular body and may be defined by distalmost edges of the body. The slot may include a proximal section and a distal section, the distal section may extend proximally from a distalmost end of the tubular body, and the proximal section may be defined by edges of the wall that extend substantially parallel to a distalmost edge of the tubular body, and the proximal section may connect to the distal section at an obtuse angle. A portion of the protrusion may be defined by and adjacent to the proximal section of the slot. The protrusion may be a first protrusion, and the tubular body may comprise a second protrusion circumferentially spaced around the tubular body from the first protrusion. The second protrusion may be defined by a second slot in the wall, the second slot being transverse to the longitudinal axis of the tubular body, and the second slot may extend proximally from the distal end of the tubular body and define a second apex at an end of the second protrusion. A distalmost surface of the protrusion may be normal to the longitudinal axis of the tubular body.

According to other aspects of the present disclosure, a medical device may include a shaft having a proximal end and a distal end. The medical device may also include a tubular body at the distal end of the shaft, and the tubular body may include a wall and a longitudinal lumen. The wall of the tubular body may include (1) a proximal portion having a proximal inner diameter and (2) a distal portion having a distal inner diameter and a plurality of protrusions, where each of the plurality of protrusions is tapered to an apex configured to penetrate tissue, wherein the plurality of protrusions are circumferentially spaced around a distal end of the tubular body, and the proximal inner diameter may equal the distal inner diameter.

The medical device may also include one or more of the features below. The apex of each of the plurality of protrusions of the tubular body may be sharp. The proximal inner diameter and the distal inner diameter may be constant from a proximal end of the tubular body to the distal end of the tubular body, and the wall may have a thickness between 2 and 10 thousandths of an inch. The tubular body may include a plurality of slots in the wall of the tubular body that extend proximally from the distal end of the tubular body. Each of the slots may include a proximal section and a distal section, and the proximal section may extend along a different path than the distal section. The proximal section of each of the slots may be substantially perpendicular to the longitudinal axis of the tubular body, and the distal section of each of the slots may be angled relative to the longitudinal axis of the tubular body.

The foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a subject. The term "proximal" refers to the end closest to the user when placing the device into the subject. For example, a proximal direction and a distal direction are identified using arrows in FIG. 1. When used herein, the terms "approximately" and "substantially" may indicate a range of values within +/−5% of a stated value.

Figure 1:
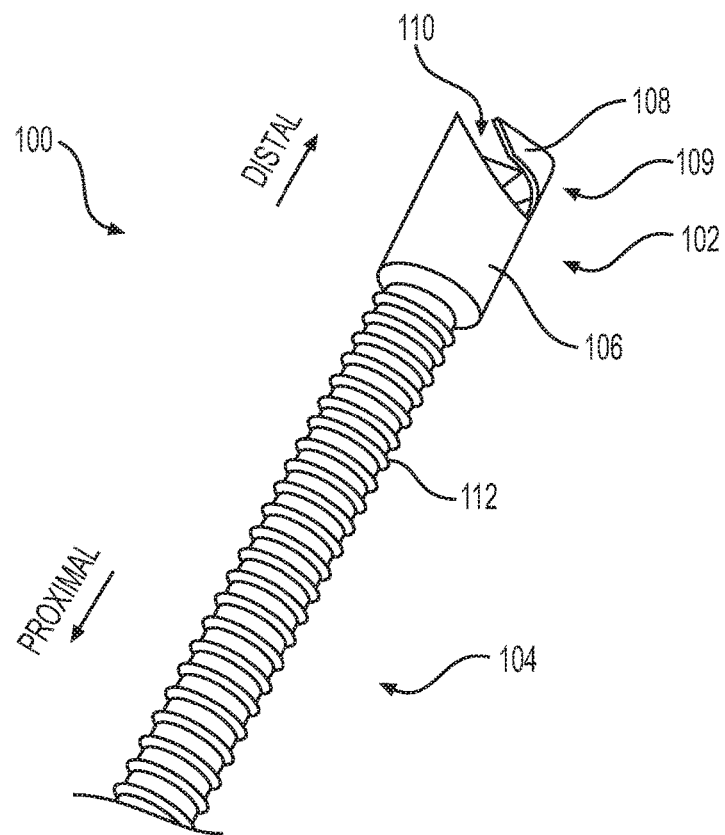
FIG. 1 illustrates a perspective view of a distal portion of an exemplary medical device, according to aspects of this disclosure.
Figure 2:
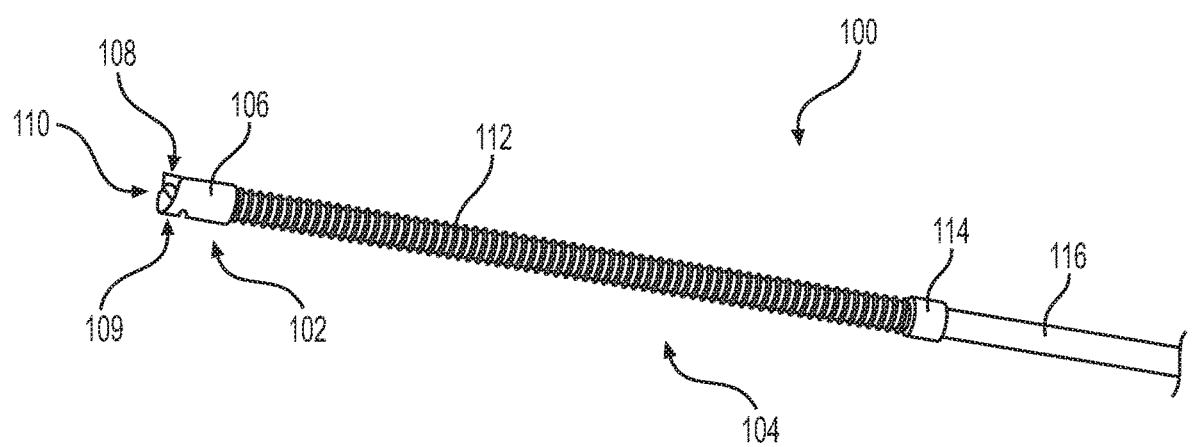
FIG. 2 illustrates a distal portion of the exemplary medical device of FIG. 1, according to aspects of this disclosure.

FIGS. 1 and 2 illustrate perspective views of a distal portion 104 of an exemplary medical device 100. Medical device 100 may include a proximal portion 300 (shown in FIG. 3) and a distal portion 104. A shaft 116 may extend from the proximal portion 300 to the distal portion 104. Distal portion 104 may include a connector 114, a distal section 112, and a distal tip 102. Connector 114 may couple shaft 116 to distal section 112, and a distal portion of distal section 112 may be coupled to distal tip 102. Distal tip 102 may include a body 106 with one or more gaps 110 in body 106 forming one or more protrusions 108. A grasping section 109 may be formed by the one or more gaps 110 and one or more protrusions 108 at a distal portion of the distal tip 102.

Figure 3:
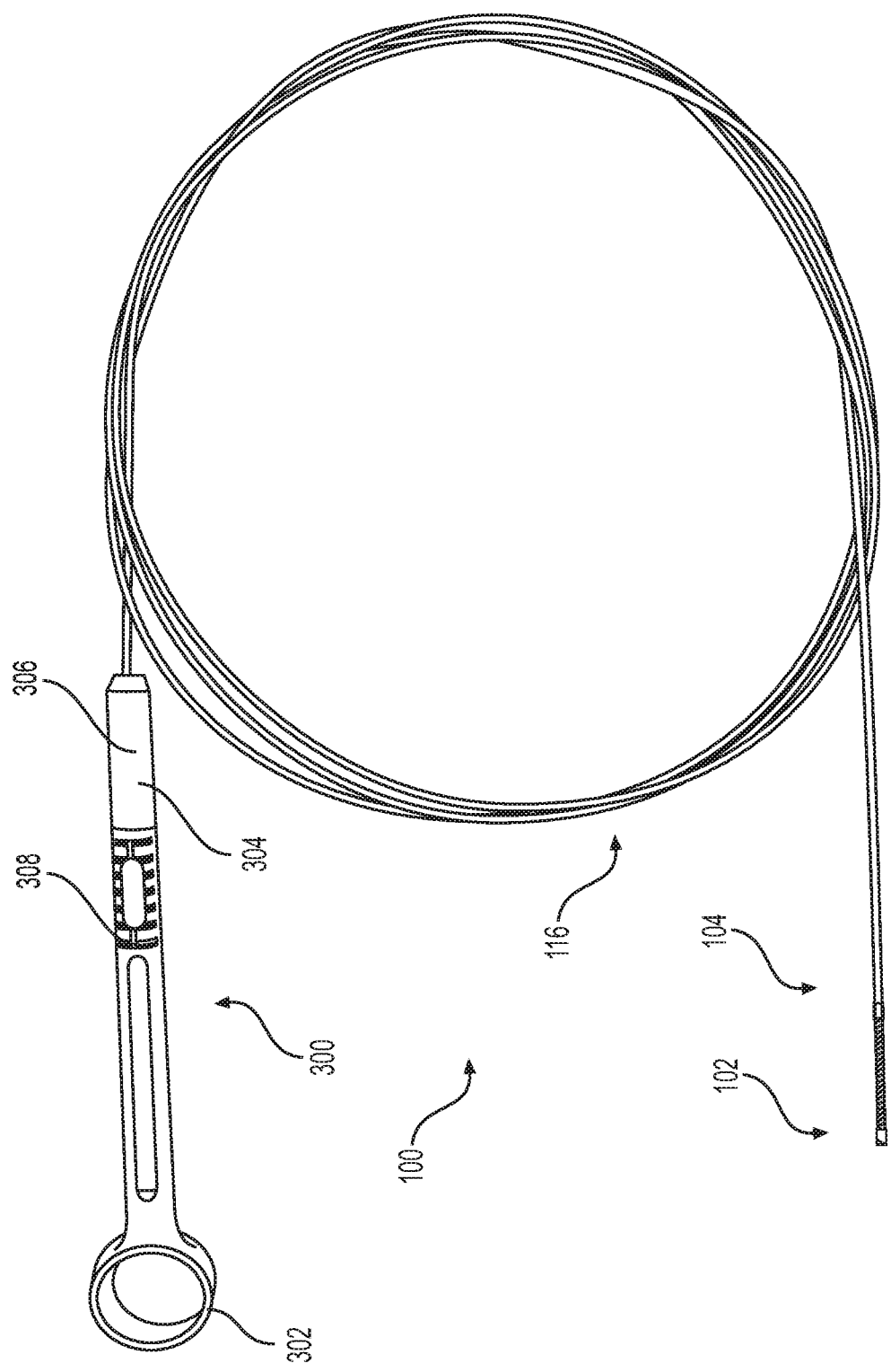
FIG. 3 illustrates a perspective view of the exemplary medical device of FIG. 1, according to aspects of this disclosure.

FIG. 3 illustrates a perspective view of medical device 100 including distal portion 104, shaft 116, and proximal portion 300. Proximal portion includes a handle 304. Distal portion 104, which may include distal tip 102, distal section 112, and connector 114, may be coupled to shaft 116. In some examples, shaft 116 may be directly coupled to distal tip 102 without distal section 112 or connector 114.

Handle 304 may be fixedly coupled to shaft 116 at a distal section 306 of handle 304 and the distal section 306 of handle 304 may rotate shaft 116 and distal section 104 when a user rotates the distal section 306 of handle 304. Proximal portion 308 of handle 304 may be held by a user, and distal section 306 may be rotated relative to proximal section 308 allowing a user to hold handle 304 at its proximal section 308 while rotating distal section 306 to rotate distal tip 102. By having distal section 306 rotatable relative to proximal section 308 of handle 304, a user may hold medical device 100 at proximal section 308 with one hand and rotate distal tip 102 with a second hand by rotating distal section 306. Some users may hold and operate medical device 100 with a single hand, for example holding proximal section 308 with three fingers and using the other two fingers, such as an index finger and a thumb, to rotate distal section 306, thus rotating distal tip 102. This occurs without rotating the hand holding proximal portion 308 of handle 304. In other examples, distal section 306 and proximal section 308 may be fixedly coupled together, and distal tip 102 may be rotated by rotating both distal section 306 and proximal section 308 of handle 304.

Loop 302 of handle 304, also called a thumb ring or finger ring, may have a circumference large enough to accommodate the insertion of one or more fingers (for example, a thumb) of the operator into loop 302, which may facilitate holding of handle 304. In some examples, handle 304 may not include loop 302. Although FIG. 3 illustrates shaft 116 of medical device 100 in a coiled configuration (for example, for a packaging configuration), shaft 116 may be extended/straightened such that shaft 116 is not coiled or only partially coiled.

Figure 4:
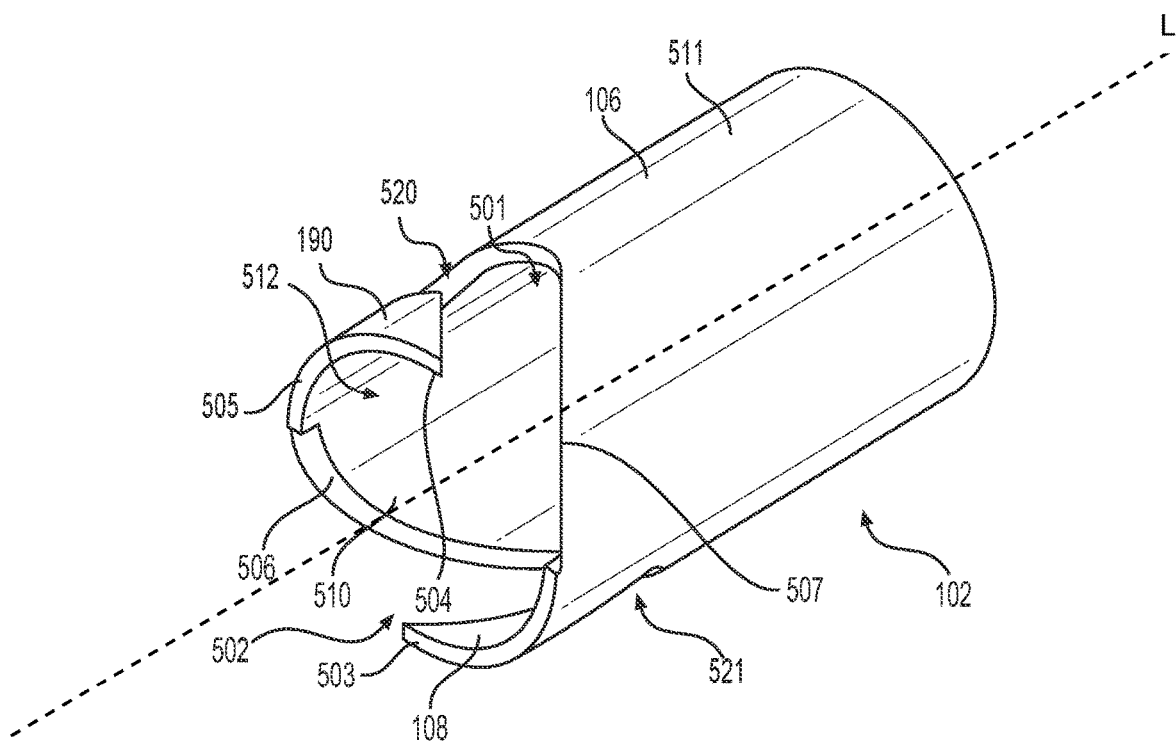
FIG. 4 illustrates a perspective view of an exemplary distal tip of the medical device of FIG. 1, according to aspects of this disclosure.
Figure 5:
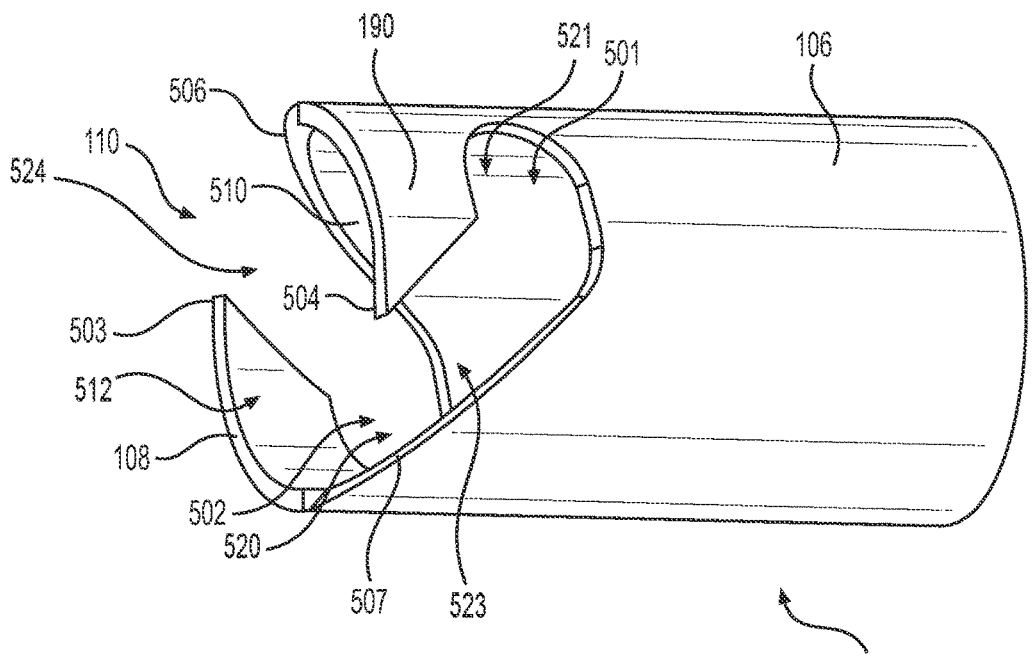
FIG. 5 illustrates a perspective view of an exemplary distal tip of the medical device of FIG. 1, according to aspects of this disclosure.

FIGS. 4 and 5 illustrate perspective views of an exemplary distal tip 102 of medical device 100. In some examples, body 106 of distal tip 102 may be hollow like a tube, or at least partially hollow, for example at least the distal portion being hollow. Body 106 may include a lumen 512 extending longitudinally through the cylindrical body 106, forming a tube having a proximal opening and a distal opening at the ends of the distal tip 102 and a cylindrical wall extending longitudinally between the proximal and distal openings at the ends of the distal tip 102. In some examples, a proximal opening of lumen 512 may be configured to receive and couple to distal section 112 or shaft 116. In other examples, distal tip 102 may include a proximal surface extending across the proximal opening and covering the proximal opening of the lumen 512. An inner surface 510 of body 106 of distal tip 102 may be a radially inner surface of body 106, define lumen 512, and extend from a proximal portion to a distal portion of distal tip 102. An outer surface 511 may extend from a proximal portion to a distal portion of distal tip 102, be on a radially outer surface of body 106, and be curved. Body 106 may be cylindrical, having a circular cross-sectional shape, In other examples, body 106 may have cross-sectional shapes other than circular, including ovular, triangular, rectangular, etc., and radially outer surface 511 may include other profiles, including multiple planar surfaces. Body 106 of distal tip 102 may include two distal surfaces 503, 505 (edges), and surfaces 503, 505 may connect inner surface 510 to outer surface 511. The surfaces 503, 505 may be separated by gaps 501, 502, and may be curved. In some examples, body 106 may have a longitudinal wall with a thickness equal to the radial distance from the longitudinal axis between edges of surface 503 and/or surface 505. In some examples, the distalmost surface of body 106 may include surfaces 503, 505. Surfaces 503, 505 may be part of each protrusion 108, 190 of body 106.

Gaps 501, 502 may extend proximally from a distalmost end of body 106 adjacent surfaces 503, 505, and may be angled such that a sharp point may be formed at the end of each protrusion 108, 190. Each gap 501, 502 may form a partial helix or spiral shaped gap or hole radially through body 106 and outer 511 and inner 510 surfaces of body 106. Each gap 501, 502 may be in a longitudinal wall of body 106, and each protrusion 108, 190 may be part of the longitudinal wall of body 106. In some examples, gaps 501, 502 may form slots, flutes, and/or cutouts in body 106. In some examples, body 106 may be a tubular body and may include one or more slots transverse to a longitudinal axis of the tubular body. Each slot or gap 501, 502 may be defined by and between a gap surface 506, 507, and each gap surface 506, 507 may be positioned at a different angle than surfaces 503, 505 relative to the longitudinal axis (axis L shown as a dotted line in FIG. 4) of body 106. Each gap surface 506, 507 may be an edge of a longitudinal wall of body 106 and may be transverse to the longitudinal axis of body 106. For example, gap surfaces 506, 507 may have portions that are transverse to the longitudinal axis of body 106, while surfaces 503, 505 are perpendicular or substantially perpendicular to the longitudinal axis.

Gap surfaces 506, 507 may spiral from a distal portion of body 106, such as from surfaces 503, 505, to a proximal portion of body 106 proximal to surfaces 503, 505. Gaps 501, 502 may define points, spikes, jagged protrusions, and/or protrusions with tapered ends at a distal end of body 106. For example, gaps 501, 502 may form protrusions 108, 190 shown in FIGS. 4 and 5, which may facilitate piercing and/or grabbing tissue. Each protrusion 108, 190 may have a tapered end with a sharp point and may be configured to grasp tissue. In some examples, a sharp point may be formed by two surfaces meeting at an angle of 45° or less. In some examples, each gap 501, 502 may include two sections, a proximal section 520, 521 and a distal section 523, 524. Proximal sections 520, 521 may be positioned at the proximal end of each gap 501, 502, and may be defined by surfaces or edges that extend perpendicular or substantially perpendicular to the longitudinal axis of body 106 and/or parallel with distal surfaces 503, 505. Proximal sections 520, 521 of gaps 501, 502 may facilitate grabbing tissue by allowing tissue pierced by protrusions 108, 190 to be held in a proximal section 520, 521 of one or more of the gaps 501, 502 and prevent the tissue from sliding on one of the angled surfaces of distal sections 523, 524 of gaps 501, 502. Proximal sections 520, 521 may include rounded end surfaces that cut tissue may abut, thereby preventing medical device 100 from further cutting pierced tissue when rotated and allow tissue to be lodged or held in proximal sections 520, 521 of gaps 501, 502.

In some examples (not shown), body 106 of distal tip 102 may include only one protrusion and only one gap. In other examples, body 106 of distal tip 102 may include 2, 3, 4, 5, 6, or any other number of protrusions and corresponding gaps. For example, body 106 may include four protrusions at the distal end of body 106, and each protrusion may define a spiral shaped gap similar to gaps 501, 502 and may also include proximal and distal sections of the gaps similar to proximal sections 520, 521 and distal sections 523, 524. Protrusions 108, 190 may form sharp ends or tips configured to engage tissue. Protrusions 108, 190 may be circumferentially spaced around body 106, such as protrusions 108, 190 shown in FIGS. 4 and 5.

Referring to FIGS. 2 and 3, shaft 116 may be made of any suitable material. In some examples, shaft 116 may be a braided coil, such as a braided metal coil, and may be configured to rotate distal tip 102 without significant lag or whip when distal section 306 of handle 304 is rotated. In other examples, shaft 116 may be a solid material, such as polyether ether ketone (PEEK) or other plastic material. In some examples, distal section 112 may be part of shaft 116. In other examples, distal section 112 may be a different material than shaft 116 and may be coupled to shaft 116. Shaft 116 and distal section 112 may be configured to directly rotate distal tip 102 when distal section 306 of handle 304 is rotated. In some examples (not shown), a sheath may be positioned on the exterior surface of the shaft and extend from the proximal portion 300 of medical device 100 to the distal portion 104. Such a sheath may be moveable in the distal direction in order to slide the sheath over the distal tip 102 to protect the distal tip 102 and/or protect the environment surrounding the distal tip 102 from being unintentionally damaged by the sharp points/edges of tip 102. The sheath may protect the lumen of a medical device that medical device 100 is passed through, such as a working channel of an endoscope. The sheath may be moved proximally in order to expose the distal tip 102 for the tip 102 to engage tissue. In some examples, the sheath may be made of polytetrafluoroethylene (PTFE). In other examples, a sheath may be fixed to the exterior of shaft and terminate at a position proximal to distal tip 102.

Distal tip 102 may be formed using a metal tube such as a hypotube or rod of any size. For example, distal tip 102 may be formed of stainless steel, a material configured to resist bending or yielding, or any other suitable material. In some examples, a metal rod is drilled to create a tube prior to cutting and forming protrusions, such as protrusions 108, 190. The thickness of the wall of the tube may vary depending on the desired stiffness of the body of the distal tip. In some examples, the outer diameter of the metal rod may be less than 1 inch, less than 0.1 inches, or approximately 0.093 inches. The outer diameter of the metal rod may form outer surface 511. In some examples, the thickness of the wall of the tube may be between 5 and 10 thousandths of an inch. Gaps in the tube, such as gaps 501, 502, may be formed by cutting a distal end of the tube, forming protrusions, such as protrusions 108, 190. In some examples, the distal end of the tube may be fluted to form sharp points at portions of the wall of the tube. The distal end of medical device 100, including distal tip 102, may be configured to fit through a working channel of an endoscope or other medical device. In some examples, the distal end of medical device 100 may be configured to fit down a working channel of 2.8 millimeters inner diameter.

In use of any of the aforementioned embodiments of medical devices, a user may locate a treatment site (such as a tumor, lesion, or other tissue) present in a subject's body using an endoscope or other tool. The endoscope may include an image sensor at its distal end to provide direct visualization of the treatment site. Any of the aforementioned medical devices may be inserted through the endoscope until the distal portion of the medical device is at the treatment site. The user may press the distal end of the medical device, which may include one or more protrusions and one or more gaps, against tissue to engage the tissue. While holding a handle of the medical device at a proximal portion of the handle, the user may rotate the distal portion of a handle of the medical device clockwise or counterclockwise in order to rotate the medical device's distal tip, causing the distal tip of the medical device to rotate and engage tissue of the patient. For example, protrusions of the medical device may pierce or cut the tissue and the tissue may be held by the one or more protrusions that have pierced or cut the tissue of the patient. In some examples, the medical device may be rotated between approximately 180° and approximately 360° to engage tissue of the patient. In some examples, tissue may be positioned at a proximal section of a gap in the distal tip of the medical device. Once the one or more protrusions of the medical device engage the tissue, the tissue may be pulled proximally by the user pulling the handle of the medical device proximally. In some examples, the one or more protrusions may engage the tissue by piercing the tissue and lodging the tissue in a proximal section of a gap in the distal tip, effectively hooking the tissue.

In some examples, the user may also use the medical device as a bore and may cut into tissue of the patient by continuously rotating the medical device and pushing the device in a distal direction. It should be understood that the user may move one or more pieces of tissue by engaging tissue with the distal end of the medical device so the distal end of the medical device and the tissue move in tandem. In some examples, the user may remove the distal end of the medical device from the working channel of the endoscope to remove the engaged tissue from the patient's body. Using the medical devices described herein, a user may grab tissue effectively and may avoid tissue slipping from the medical device due to excessive saliva, mucus, or other bodily fluid present on the tissue or at the surgical site.

It should be understood that one or more of the aspects of any of the medical devices described herein may be used in combination with any of the other aspects. It also should also be understood that one or more aspects of any of the medical devices described herein may be used for cutting, grabbing, holding, moving, dissecting, or treating tissue in any part of the human body. For example any of the medical devices described herein may be used in medical procedures such as for endoscopic submucosal dissection (ESD), cancer treatment, and/or other procedures where grabbing, moving, holding, or removing tissue is needed.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

We claim:

1. A medical device, comprising:
a shaft having a proximal end and a distal end;
a handle coupled to the proximal end of the shaft; and
a body at the distal end of the shaft, the body having a wall defining a lumen within the body, the lumen having a longitudinal axis, wherein the wall includes a protrusion at a distal end of the body, the protrusion being defined by a gap in the wall and having a sharp portion configured to grasp tissue, wherein the gap extends proximally from the distal end of the body, and a first edge of the wall defining the gap meets a second edge of the wall defining the gap at an obtuse angle, and wherein each of the first edge and the second edge faces a proximal direction, wherein the gap in the wall has an open distal end at a distal most end of the body and is defined by distalmost edges of the body, wherein a portion of the body is distal to the second edge.

2. The medical device of claim 1, wherein the protrusion is a first protrusion, and the gap is a first gap, and the body comprises a second protrusion circumferentially spaced around the body from the first protrusion, the second protrusion being defined by a second gap in the wall and having a second sharp portion configured to grasp tissue, wherein the second gap extends proximally from the distal end of the body, and a third edge of the wall defining the second gap meets a fourth edge of the wall defining the second gap at an obtuse angle, wherein the first protrusion and the second protrusion each extends to a distalmost end of the body.

3. The medical device of claim 2, wherein the first gap includes a first proximal section and a first distal section, the first distal section extends proximally from the distal end of the body and is defined by at least the first edge, and the first proximal section is defined by at least the second edge; and
wherein the second gap includes a second proximal section and a second distal section, the second distal section extends proximally from the distal end of the body and is defined by at least the third edge, and the second proximal section is defined by at least the fourth edge; and
wherein the first proximal section is positioned at an opposing side of the body as the second proximal section.

4. The medical device of claim 2, wherein a fifth edge extends proximally from the distal end of the body, defines the first gap, forms a portion of the second protrusion, and extends substantially parallel to the first edge; and wherein a sixth edge extends at an obtuse angle from a proximal end of the fifth edge.

5. The medical device of claim 1, wherein the gap includes a proximal section and a distal section, the distal section extends proximally from the distal end of the body and is defined by at least the first edge, and the proximal section is defined by at least the second edge, wherein the proximal section comprises a third edge facing a distal direction.

6. The medical device of claim 5, wherein the protrusion includes an apex formed by two surfaces meeting at an angle less than 45°, and wherein a portion of the second edge is spaced from and faces the third edge.

7. The medical device of claim 5, wherein the proximal section is defined at least partially by a rounded edge of the wall and is configured to hold tissue.

8. The medical device of claim 1, wherein a diameter of the body at the protrusion is the same as a diameter of the body proximal of the protrusion.

9. A medical device, comprising:
a shaft having a proximal end and a distal end; and
a tubular body at the distal end of the shaft, the tubular body including a wall, wherein the wall includes a protrusion at a distal end of the tubular body, the protrusion defined by a slot in the wall, the slot being transverse to a longitudinal axis of the tubular body, wherein the slot extends proximally from the distal end of the tubular body and defines an apex at an end of the protrusion;
wherein the slot includes a proximal section and a distal section, the distal section extends proximally from a distalmost end of the tubular body, and the proximal section is defined by a first edge, a second edge, and a third edge of the wall, wherein the first edge and the third edge each extends substantially parallel to a distalmost edge of the tubular body, and wherein the first edge and the third edge face each other.

10. The medical device of claim 9, wherein the apex includes a sharp point configured to pierce tissue, and wherein a portion of the body is spaced from and distal to the third edge.

11. The medical device of claim 9, wherein the slot in the wall has an open distal end at a distalmost end of the tubular body and is defined by distalmost edges of the body, and a closed proximal end positioned distal from the proximal end of the tubular body, wherein the closed proximal end is formed by the second edge.

12. The medical device of claim 9, wherein a portion of the protrusion is defined by and is adjacent to the proximal section of the slot.

13. The medical device of claim 9, wherein the protrusion is a first protrusion, and the tubular body comprises a second protrusion circumferentially spaced around the tubular body from the first protrusion, the second protrusion being defined by a second slot in the wall, the second slot being transverse to the longitudinal axis of the tubular body, wherein the second slot extends proximally from the distal end of the tubular body and defines a second apex at an end of the second protrusion; wherein the second slot includes a proximal section and a distal section, the distal section of the second slot extends proximally from the distalmost end of the tubular body, and the proximal section of the second slot is defined by defined by a fourth edge, a fifth edge, and a sixth edge of the wall, wherein the fourth edge and the sixth edge each extends substantially parallel to the distalmost edge of the tubular body, and wherein the fourth edge and the sixth edge face each other.

14. The medical device of claim 9, wherein a distalmost surface of the protrusion is normal to the longitudinal axis of the tubular body.

15. A medical device, comprising:
a shaft having a proximal end and a distal end; and
a tubular body at the distal end of the shaft, the tubular body including a wall and a longitudinal lumen, wherein the wall of the tubular body includes (1) a proximal portion having a proximal inner diameter and (2) a distal portion having a distal inner diameter and a plurality of protrusions, where each of the plurality of protrusions is tapered to an apex configured to penetrate tissue, wherein the plurality of protrusions are circumferentially spaced around a distal end of the tubular body, and wherein the proximal inner diameter equals the distal inner diameter;
wherein the tubular body includes a plurality of slots in the wall of the tubular body that extend proximally from the distal end of the tubular body, wherein each of the slots includes a proximal section and a distal section, the proximal section extending at an obtuse angle relative to the distal section;
wherein each of the plurality of protrusions is distal to and longitudinally aligned with a distal-facing edge of the tubular body.

16. The medical device of claim 15, wherein the apex of each of the plurality of protrusions of the tubular body is sharp, and wherein each of the plurality of protrusions includes a first proximally-facing edge and a second proximally-facing edge extending at an obtuse angle from the first proximally-facing edge.

17. The medical device of claim 16, wherein each of the proximal sections of the plurality of slots is defined by at least one second proximally-facing edge that is substantially parallel to a distalmost edge of the tubular body.

18. The medical device of claim 15, wherein the proximal inner diameter and the distal inner diameter are constant from a proximal end of the tubular body to the distal end of the tubular body, and the wall has a thickness between 5 and 10 thousandths of an inch.

19. The medical device of claim 15, wherein the proximal section of each of the slots is substantially perpendicular to the longitudinal axis of the tubular body, and wherein the distal section of each of the slots is angled relative to the longitudinal axis of the tubular body.

* * * * *